United States Patent
Federici et al.

(10) Patent No.: US 8,237,452 B2
(45) Date of Patent: *Aug. 7, 2012

(54) METHODS AND APPARATUS FOR THE NON-DESTRUCTIVE DETECTION OF VARIATIONS IN A SAMPLE

(75) Inventors: John Francis Federici, Westfield, NJ (US); Rose M. Federici, Westfield, NJ (US)

(73) Assignee: New Jersey Institute of Technology, Newark, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/024,406

(22) Filed: Feb. 10, 2011

(65) Prior Publication Data
US 2011/0127432 A1    Jun. 2, 2011

Related U.S. Application Data

(63) Continuation of application No. 11/965,045, filed on Dec. 27, 2007, now Pat. No. 7,906,975.

(60) Provisional application No. 60/898,208, filed on Jan. 30, 2007.

(51) Int. Cl.
G01R 27/04 (2006.01)
G01J 5/02 (2006.01)

(52) U.S. Cl. ............................ 324/639; 250/341.1

(58) Field of Classification Search .......... 324/639
See application file for complete search history.

(56) References Cited

U.S. PATENT DOCUMENTS

| | | | |
|---|---|---|---|
| 5,038,039 A | 8/1991 | Wong | |
| 5,710,430 A | 1/1998 | Nuss | |
| 6,341,521 B1 | 1/2002 | Bartolomey | |
| 6,479,822 B1* | 11/2002 | Nelson et al. | 250/341.1 |
| 6,717,428 B1 | 4/2004 | Spica | |
| 7,012,427 B2 | 3/2006 | Augustine | |
| 2002/0067480 A1 | 6/2002 | Takahashi | |
| 2004/0010196 A1 | 1/2004 | Wang | |
| 2004/0232052 A1 | 11/2004 | Call et al. | |
| 2005/0082479 A1* | 4/2005 | Wallace et al. | 250/330 |
| 2005/0156110 A1* | 7/2005 | Crawely | 250/338.1 |
| 2006/0049356 A1 | 3/2006 | Shen et al. | |
| 2007/0235658 A1* | 10/2007 | Zimdars et al. | 250/390.07 |

FOREIGN PATENT DOCUMENTS

WO 0148457 A1 7/2001

OTHER PUBLICATIONS

M. Koch et al., "THz-imaging: A New Method for Density Mapping of Wood" Wood Science and Technology, vol. 32, No. 6, Dec. 1, 1998.

(Continued)

*Primary Examiner* — Jeff Natalini
(74) *Attorney, Agent, or Firm* — Timothy X. Gibson, Esq.; Gibson & Dernier LLP

(57) ABSTRACT

Non-invasive THz spectroscopic apparatus and methods are provided for detecting and/or identifying constituents such as variations in a structural entity where chemical or biological entities can reside. Position dependent scattering of THz radiation is employed to image voids and defects in the internal structure of samples, enabling the determination of contamination, spoilage or readiness of products such as wine in sealed containers.

12 Claims, 7 Drawing Sheets

OTHER PUBLICATIONS

Takeshi Yasui, "Sensitive Measurement of Water Content in Dry Material Based on Low-Frequency Terahertz Time-Domain Spectroscopy" Proceedings of SPIE, vol. 6024, pp. 60240A-60240A-6, Jan. 1, 2006.
Watanabe Y, et al., "Component Analysis of Chemical Mixtures using Terahertz Spectroscopic Imaging" Optics Communications, North-Holland Publishing Co. vol. 234, No. 1-6,pp. 125-129, Apr. 15, 2004.
Yew Li Hor et al., "Nondestructive Evaluation of Cork Enclosures Using Terahertz/Millimeter Wave Spectroscopy and Imaging" Applied Optics, Optical Society of America vol. 47, No. 1, pp. 72-78, Jan. 1, 2008.
Yew Li Hor et al., Terahertz Study of Trichloranisole by Time-Domain Spectroscopy Laser Science, p. 1 Sep. 16, 2007.
Supplementary European Search Report for application EP07869976, dated Oct. 19, 2011.
International Search Report and Written Opinion of PCT/US07/088932, issued Jul. 1, 2008.
Chang, J., et al.: "Cork quality classification system using a unified image processing and fuzzy-neural network methodology," IEEE Transactions on Neural Networks, vol. 8, No. 4, Jul. 1997, pp. 964-974.
Juanola, R., et al.: "Evaluation of an extraction method in the determination of the 2,4,6-trichloroanisole content of tainted cork," Journal of Chromatography A, 953 (2002) 207-214.
Lizarraga, E., et al.: "Determination of chloroanisole compounds in red wine by headspace solid-phase microextraction and gas chromatography-mass spectrometry," Journal of Chromatography A, 1052 (2004) 145-149.
Brunetti, A., et al.: "Cork quality estimation by using Compton tomography," Nuclear Instruments and Methods in Physics Research B 1996 (2002) 161-168.
Zimdars, D., et al.: "Time domain terahertz detection of flaws within space shuttle sprayed on foam insulation," 2004 OSA/CLEO 2004.
Chua, H.S., et al.: "Terahertz time-domain spectroscopy of wheat grain," Spectroscopy and material properties, 2004 IEEE, pp. 399-400.
Chua, H.S., et al.: "Terahertz time-domain spectroscopy of crushed wheat grain," 2005 IEEE, pp. 2103-2106.
Hadjiloucas, S., et al.: "Measurements of leaf water content using terahertz radiation," IEEE Transactions on Microwave Theory and Techniques, vol. 47, No. 2, Feb. 1999, pp. 142-149.
Hadjiloucas, S., et al.: "Analysis of spectroscopic measurements of leaf water content at terahertz frequencies using linear transforms," vol. 19, No. 12/Dec. 2002/J. Opt. Soc. Am. A, pp. 2495-2509.
Reid, M., et al.: "Terahertz birefringence and attenuation properties of wood and paper," Applied Optics, vol. 45, No. 12, Apr. 20, 2006, pp. 2766-2772.
Strachan, C.J., et al., "Using terahertz pulsed spectroscopy to study crystallinity of pharmaceutical materials," Chemical Physics Letters 390, (2004) pp. 20-24.
Venables, D.S., et al.: "Spectroscopy and dynamics of mixtures of water with acetone, acetonitrile, and methanol," Journal of Chemical Physics, vol. 113, No. 24, Dec. 22, 2000, pp. 11222-11236.
Federici, J.F., et al.: THz imaging and sensing for security applications—explosives, weapons and drugs, Semicond. Sci. Technol. 20 (2005) S266-S280.
Beard, M.C., et al.: "Terahertz Spectroscopy," J. Phys. Chem. B 2002, 106, 7146-7159.
Huang, F., et al.: "Terahertz study of 1,3,5-trinitro-s-triazine by time-domain and Fourier transform infrared spectroscopy," Applied Physics Letters, vol. 85, No. 23, Dec. 6, 2004, pp. 5535-5537.
Karlsson, S., et al.: "Formation of 2,4,6-trichlorophenol and 2,4,6-trichloroanisole during treatment and distribution of drinking water," Wat. Sci. Tech., vol. 31, No. 11, pp. 99-103, 1995.
Prescott, J., et al.: "Estimating a "consumer rejection threshold" for cork taint in white wine," Food Quality and Preference 16 (2005) 345-349.
Miki, A., et al.: "Identification of 2,4,6-trichloroanisole (TCA) causing a musty/muddy off-flavor in sake and its production of rice koji and moromi mash," Journal of Bioscience and Bioengineering, vol. 100, No. 2, 178-183, 2005.
Aung, L.H., et al.: "Investigations into the origin of chloroanisoles causing musty off-flavor of raisins," J. Agric. Food Chem. 1996, 44, 3294-3296.
Mittleman, D.M., et al.: "T-ray tomography," Optics Letters, vol. 22, No. 12, Jun. 15, 1997, pp. 904-906.
Yasuda, T., et al.: "Real-time two-dimensional terahertz tomography of moving objects," Optics Communications 267 (2006) 128-136.
Zhong, H., et al.: "Nondestructive defect identification with terahertz time-of-flight tomography," IEEE Sensors Journal, vol. 5, No. 2, Apr. 2005, pp. 203-208.
E. Herve, S. Price, G. Burns, P. Weber, presented at the ASEV Annual Meeting, Reno, Nevada, Jul. 2, 1999. http://www.corkqc.com/asev/asev2-2.htm.
D. Zimdars, J.S. White, G. Stuk, A. Chernovsky, G. Fichter, and S. Williamson, "Large area terahertz imaging and non-destructive evaluation applications," Insight-Non-Destructive Testing and Condition Monitoring 48, 537-539 (2006).
J. F. Federici, D. Gary, R. Barat, Z.-H. Michalopoulou, 'Detection of Explosives by Terahertz Imaging', in Counter-Terrorism Detection Techniques of Explosives Jehuda Yinon Ed. (Elsevier, 2007).
F. C. Delucia, "Spectroscopy in the Terahertz Spectral Region", in Sensing with Terahertz Radiation, D. Mittleman Ed. (Springer, 2003).
A. Nystrom, A. Grimvall, C. Krantz-Rulcker, R. Savenhed, K. Akerstrand, "Drinking water off-flavour caused by 2,4,6-trichloroanisole," Water Science and Technology 25, No. 2, 241-49 (1992).
C. Silva Pereira, J.J. Figueiredo Marques, M.V. San Romao, "Cork taint in wine: Scientific knowledge and public perception—A critical review," Critical Reviews in Microbiology 26(3), 147-62 (2000).
A.P. Pollnitz, K.H. Pardon, D. Liacopoulos, G.K. Skouroumounis, M.A. Sefton, "The analysis of 2,4,6-trichloroanisole and other chloroanisoles in tainted wines and corks," Australian J. Grape and Wine Research 2, 184-90 (1996).
J. Gunschera, F. Fuhrmann, T. Salthammer, A. Schulze, E. Uhde, "Formation and emission of chloroanisoles as indoor pollutants," Environmental Science and Pollution Research 11(3), 147-51 (2004).
D. Mittleman, "Terahertz Imaging" in Sensing with Terahertz Radiation, D. Mittleman Ed. (Springer, 2003).
International Search Report and Written Opinion for corresponding PCT application PCT/US2007/088932, Jul. 1, 2008 (Form PCT/ISA/237.
International Preliminary Report on Patentability for corresponding PCT application PCT/US2007/088932, Aug. 4, 2009 (Form PCT/IB/326/373/PCT/ISA/237).
Office Action for corresponding U.S. Appl. No. 11/965,045, dated Dec. 10, 2009.
Office Action for corresponding U.S. Appl. No. 11/965,045, dated Jul. 19, 2010.

* cited by examiner

METHODS AND APPARATUS FOR THE NON-DESTRUCTIVE DETECTION OF VARIATIONS IN A SAMPLE

CROSS-REFERENCE TO RELATED APPLICATIONS

This application is a continuation of U.S. patent application Ser. No. 11/965,045 filed Dec. 27, 2007 and claims the benefit of U.S. Provisional Patent Application No. 60/898,208, filed Jan. 30, 2007, the entireties of which are incorporated herein by reference.

FIELD OF THE INVENTION

This invention relates to methods and apparatus for performing terahertz (herein referred to as "THz") spectroscopy. More specifically, the invention relates to the detection of one or more constituents, such as variations in structural entities or chemical or biological entities in a sample such as wine corks, bottled wine or other sealed containers or goods by analyzing structural variations or voids in the sealing apparatus or cork.

BACKGROUND OF THE INVENTION

Many products such as wine and other products are typically stored in glass bottles and sealed with a stopper made of natural or synthetic cork. Natural cork is acquired from the Cork Oak (Quercus suber) predominately in Portugal and other countries surrounding the Mediterranean Sea. It is utilized in a variety of products including cork stoppers for wine and other beverages. As an enclosure for liquids, cork has the desirable properties of being impermeable to liquids and gases, as well as compressible. The quality of cork enclosures is determined by the presence and size of defects, voids, or cracks. Methods of non-destructive evaluation (NDE) of corks include visible inspection of visible cracks and defects either by human experts or camera systems, chemical analysis (including cork soaks) for the presence of 2,4,6-trichloro-anisole (TCA), and x-ray tomography.

Prior to bottling, the cork may be treated with chlorinated chemicals to kill bacteria. However, not all of the bacteria are killed. The surviving bacteria can spoil the wine through various mechanisms. The most prevalent and widely understood is the conversion of residual chlorinated compounds in treated cork by bacteria to TCA. After bottling, the TCA leaches into the wine giving it a musty, mushroom flavored taint. This type of spoilage is called cork taint, "corking" or "corked wine". The severity can range from a lack of aftertaste (or "finish") to a taste and aroma of mold or wet cardboard. Other mechanisms for wine spoilage include the presence of 2-methoxy-3,5-dimethylpyranzine (herein referred to as "MDMP"), phenol, and contamination of "clean" corks by other sources of mold or bacteria that are present in the bottling process. M. A. Sefton and R. F. Simpson, "Compounds causing cork taint and the factors affecting their transfer from natural cork closures to wine—a review", *Australian Journal of Grape and Wine Research* 11, 226-240 (2005).

"Corking" affects all types and qualities of wines, typically spoiling 3%-5% of all wines that use natural cork as a stopper. The problem of "corked" wine is even more insidious as there is no visual indication that a particular cork prior to bottling will result in cork taint or that a previously bottled wine has been "corked". Therefore consumers, collectors, auction houses, wine producers, and/or wine bottlers have no way of determining whether the wine is "corked" until they have already purchased and opened the bottle. This problem could be alleviated, however, if the wine bottle could be tested before it is purchased to see if it contains the bacteria responsible for "corking" the wine. A related issue intrinsic to wine producers and wine bottlers is determining whether the cork is tainted prior to being used as a sealing apparatus or whether the cork has a high likelihood of developing taint after bottling. Accordingly wine producers and wine bottlers would greatly benefit from a non-destructive method and apparatus to determine the presence of taint or the likelihood of the cork developing taint prior to using the cork as a sealing apparatus.

Most corks are punched with the long axis of the cork perpendicular to the lenticels. The lenticels allow for the interchange of gases between the atmosphere and in the interior structure of the cork tree. It has been shown that TCA does not quickly permeate down the length of the cork, but propagates much more quickly perpendicular to the long axis. Consequently, only when contaminated parts of the cork are in direct contact with the wine (approximately the first few millimeters of cork) does transfer of TCA into the wine take place. While there are several screening methods used by wine companies to screen cork closures, most notably, soaking the corks in wine and subsequent testing based on sensory assessments or analytic chemical analysis, there is currently no cork screening method that has been demonstrated to accurately predict the level of taint in a bottle of wine. In addition, presently available methods are slow and only test a representative selection of the corks to be used in bottling because these methods are destructive. Accordingly, since all the corks are not tested individually, there may be a percentage of tainted cork that is not detected that is ultimately used in the bottling process.

Electromagnetic radiation in the THz frequency lies between the far infrared (which is generated by optical means) and microwave (which is generated by electrical means) regions of the electromagnetic spectrum. Because THz waves lie at the edge of the capabilities of both electrical and optical wave generation techniques, it was previously difficult, if not impossible, to generate THz waves needed for THz spectroscopy. Advances in the art have been able to produce radiation in the THz spectrum that could be used for THz spectroscopy. THz radiation is readily transmitted through most non-metallic and non-aqueous mediums, thus enabling THz systems to "see through" concealing barriers such as plastic packaging, corrugated cardboard, clothing, shoes, book bags, glass, etc. in order to probe the materials contained within. This has given rise to a whole host of applications for spectroscopy in this region, including the detection of biological weapons and explosives, non-destructive testing of pharmaceutical coatings, biomedical imaging, atmospheric gas detection, chemicals in crystalline form and materials identification.

SUMMARY OF THE INVENTION

The present inventors have surprisingly found that terahertz (THz) spectroscopy can be used to detect the presence of a variety of constituents including structural entities and variations thereof including but not limited to voids, structures, anomalies, defects, density variations or locations in the sample or cork in which chemical entities such as TCA and MMDA, or biological entities such as bacteria or mold could exist or propagate, which could ultimately result in tainted wine.

Since the majority of wines are bottled using natural cork, devices and/or systems that can non-destructively detect a variety of constituents that naturally or unnaturally occur that are contained in the sample, including structural entities such as voids, structures, anomalies, defects, density variations or locations in the cork in which bacteria, chemicals or mold could exist or propagate, as well as the chemical or biological entities themselves that are responsible for "corking", would be of tremendous use for wine producers, distributors, collectors, restaurants, etc.

THz spectroscopic devices, apparatus and methods are provided that are adapted to identify wine bottles which are potentially "corked" prior to bottling and/or those "corked" after bottling but before the bottle is purchased and opened.

In one or more embodiments, the present invention provides devices, systems and methods using THz spectroscopy for detecting and/or identifying a variety of naturally or unnaturally occurring constituents including but not limited to, structural entities and variations in the structural entities such as voids, structures, anomalies, defects, density variations or locations in samples such as cork and wine bottles in which biological or chemical entities could exist or propagate, as well as the detection of the chemical or biological entities, contaminants or substances themselves, in a sample such as a sealed container, or in a sealing apparatus.

In accordance with one aspect of the present invention an apparatus is provided that analyzes the variations in the structural entity of a sample such as a cork or sealing apparatus to detect constituents such as voids, structures, anomalies, defects, density variations or locations in the cork in which various other constituents (which may also be identified herein alternatively as contaminants, subconstituents or entities), such as chemical or biological entities such as bacteria or mold could exist or propagate.

In accordance with a further aspect methods are provided for analyzing the variations in the structural entity of a sample such as a cork or sealing apparatus to detect constituents such as voids, structures, anomalies, defects, density variations or locations in the cork in which various other constituents could exist or propagate. The location and density of constituents such as but not limited to lenticels impact the mobility of biological or chemical entities in the cork as well as provide potential locales for biological entities such as microorganisms to generate chemicals or other biological entities. Therefore, by characterizing the internal structure of an individual cork, the probability of cork taint can be determined.

In one embodiment the methods provided herein enable the prediction or estimation of the likelihood that contaminants are present or may become present in a sample. An increase in the number of potential locations indicates an increase in the likelihood that the wine is corked or may become corked. Similarly, the methods herein enable the skilled artisan to test a sample such as a cork for structural variations such as voids, structures, anomalies, defects, density variations or locations in the cork in which TCA or some other manifestation (e.g. MDMP, mold, bacteria) is growing or could grow before it is used as a stopper for the wine bottle. In one embodiment the identification of the distinct THz absorption peaks for structural variations such as voids, structures, anomalies, defects, density variations or locations in the cork or sample are employed to predict or estimate the likelihood that contaminants are present or may become present. Methods may include identifying, categorizing and/or analyzing data, such as a change in radiation, or one or more distinct THz absorption values, peaks or spectra associated with the various structural variations in the sample or cork in which contaminants that promote spoilage could exist or propagate. The terms data, change in radiation, THz absorption values, peaks or spectra are used interchangeably in the current disclosure.

In one embodiment the methods and apparatus are used and applied to the non-destructive evaluation of cork. Using a time-domain THz spectroscopy and imaging system, THz transmission images are generated in the 0.1-2 THz range. The presence of voids, cracks and defects in the cork are evident in the THz image due to enhanced scattering of THz radiation. Furthermore, the cork's grain structure can be imaged. Analysis of the spectral properties of the cork shows that the THz absorbance can be modeled by a power law. An application of Mie scattering in the low scattering region qualitatively fits the observed spectral properties.

BRIEF DESCRIPTION OF THE DRAWINGS

To assist those of ordinary skill in the relevant art in making and using the subject matter hereof, reference is made to the appended drawings, wherein:

FIG. 4a: 0.1-0.3 THz; FIG. 4b: 0.3-0.5 THz; FIG. 4c: 0.5-0.8 THz; and FIG. 4d 0.8-1.0 THz. Each pixel in the images is 500 μm square. The overall size of the THz cork image is ~19 mm;

FIG. 6(a) depicts the measured THz time-domain waveform (gray) through a 4.4 mm thick cork sample. The reference waveform (black) is taken with the sample removed. FIG. 6(b) depicts corresponding amplitude as a function of frequency after Fourier transforming the time-domain data. Sharp structures near 0.57, 0.7, 1.1 THz and other frequencies in the reference waveform are artifacts of absorption by water vapor in the atmosphere;

FIG. 8 contains visible and THz images of a cork sample, wherein FIG. 8(a) is a photograph of a front view of the cork sample; FIG. 8(b) is a photograph of a rear view of the cork sample; FIG. 8(c) is a THz image of the cork sample; and FIG. 8(d) is a close-up of a portion of detail identified in the square in the THz image of FIG. 8(c);

FIG. 9 contains visible and THz images of a cork sample, wherein FIG. 9(a) is a photograph of a front view of the cork sample; FIG. 9(b) is a photograph of a rear view of the cork sample; and FIG. 9(c) is a THz image of the cork sample;

FIG. 10 contains visible and THz images of a cork sample, wherein FIG. 10(a) is a photograph of a front view of the cork sample; FIG. 10(b) is a photograph of a rear view of the cork sample; and FIG. 10(c) is a THz image of the cork sample;

Figure 1:
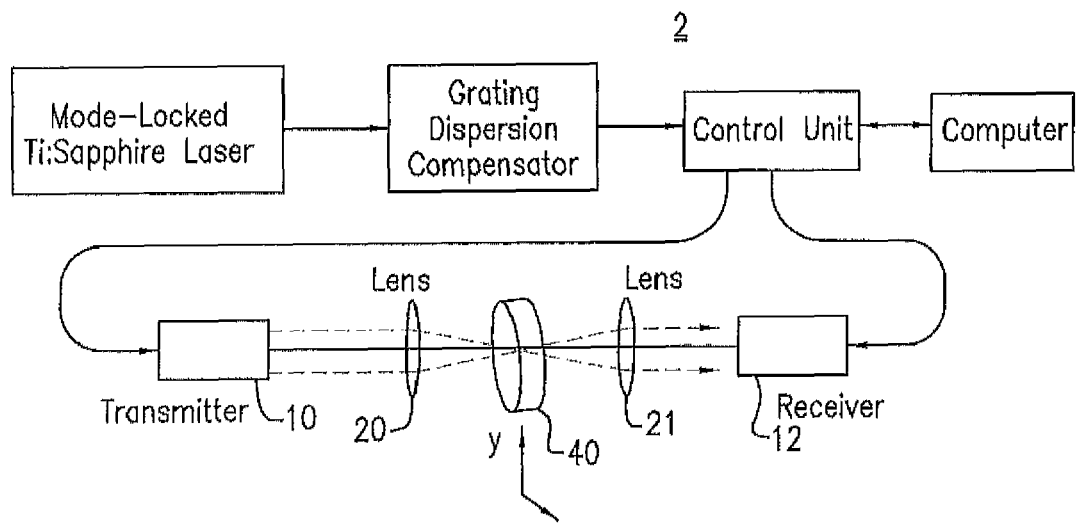
FIG. 1 depicts a schematic of a THz transmission system to measure THz spectra through a sample such as cork in accordance with at least one embodiment of the present invention.

It should be noted that the appended drawings illustrate only typical embodiments of this invention and are therefore not to be construed as limiting of its scope, for the invention may admit to other equally effective embodiments. Where possible, identical reference numerals have been inserted in the figures to denote identical elements.

DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

THz radiation is readily transmitted through most non-aqueous, non-metallic materials. Constituents such as structural entities and variations thereof such as voids or density variations as well as the chemical and biological entities that can exist or propagate in those structural entities can be detected by THz radiation. By identifying and categorizing signatures of structural variations within the cork in which the chemical or biological entities can exist or propagate which are responsible for "corked" wine, THz spectroscopy can be used to determine the potential for individual corks to spoil a wine prior to bottling, or spoilage prior to uncorking or opening a wine bottle.

Now referring to FIG. 1, in one embodiment an apparatus 2 is shown that is adapted to detect, identify, and/or quantify structural entity constituents or a constituent in a sample 40 by THz spectroscopy, preferably prior to the sample 40 being inserted into a container. Apparatus 2 includes a radiation source 3, grating dispersion compensator 5, control unit 7, transmitter 10, receiver 12 and lenses 20 and 21. A computer is optionally operably connected to apparatus 2, preferably to control unit 7. Radiation from the THz transmitter (THz TX) 10 propagates through the sample 40 and lenses 20 and 21 and is captured by the THz receiver (THz Rx) 12.

The radiation source 3 may be any suitable means of generating a signal or terahertz frequency such as but not limited to a laser, which may be used to generate and/or detect pulses of THz radiation. For example, a mode-locked Ti:sapphire laser may be employed. Alternate embodiments may include micro-fabricated antenna structures to detect pulses of THz radiation. As will be apparent to those having skill in the art, the transmitter 10 may include the radiation source 3, grating dispersion compensator 5, control unit 7 in a single unit. The receiver 12 is any suitable means of receiving and processing the terahertz radiation that is transmitted and passes through the sample 40.

The sample 40 to be analyzed may be, by way of example only and without limitation, a natural or synthetic cork or a wine bottle. Sample 40 is typically predominantly non-metallic and non-aqueous media.

As used herein, a constituent may be any substance that has a unique THz signature. The constituent may be any contaminant or combination of constituents or substances that are naturally occurring, or added substances that are included by design or chance. By way of example only, constituents may include structural entities, chemical entities and/or biological entities. The term constituent includes structural variations such as voids, structures, anomalies, defects, density variations or locations in the sample 40 (for example without limitation, cork) in which constituent(s) including chemical or biological entities exist or could propagate. In addition, constituents can be, by way of example only and without limitation, chemical or biological entities including but not limited to bacteria, mold, TCA, or some other manifestation (e.g. MDMP) that can be detected and monitored.

THz radiation used may vary in pulse duration and composition of spectral components. A THz pulse may have a duration in a range from about 1 femtosecond to about 100 nanoseconds. For example, a THz radiation pulse may be 1 to 100 picoseconds. The spectral components of the laser may fall within a range from about 0.01 THz to about 5.0 THz. For example, some embodiments include lasers emitting THz radiation having a spectrum in a range from about 0.1 THz to about 2.5 THz.

Lenses 20 and 21 are employed in some embodiments to focus the THz radiation. For example, the THz radiation may be focused to a 1 mm spot using one or more lenses. Samples 40 to be analyzed may be positioned to allow the focused radiation to contact the sample 40. In some embodiments, the sample 40 may be mechanically scanned using computer controlled translation stages. Radiation passing through the sample 40 may be focused onto a THz detector. In some embodiments, an image may be acquired one pixel at a time and/or may include recording a spectrum of the THz radiation at each pixel.

Figure 2:
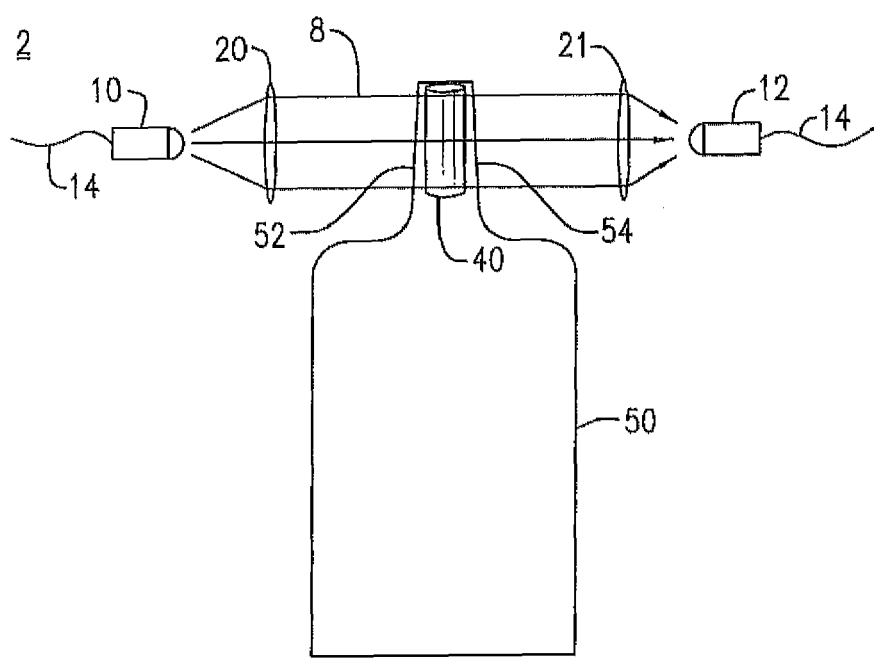
FIG. 2 depicts a schematic of a THz spectroscopy device adapted to scan a sample in accordance with at least one embodiment of the present invention.

Now referring to FIG. 2, in accordance with another embodiment, a system 2 employing THz radiation is provided for detecting, identifying, and/or quantifying one or more constituents in a sample 40. The sample 40 may be independent or acting as a sealing apparatus in a container 50. A THz transmission system 2 is adapted to measure the THz spectrum of a constituent or constituents present in a sample 50. In this embodiment, a signal or electromagnetic radiation 8 in the THz frequency range from the THz source and/or THz transmitter 10 is propagated through the sample 40. The radiation 8 that passes or propagates through the sample 40 is then captured by the THz receiver 12. The receiver 12 is preferably adapted to transmit the data and/or THz absorption peaks to an analytic device for analysis and/or computation. The data can then be compared to known THz absorption peak spectra of various constituents to determine which, if any, constituents are present in the sample 40.

In one embodiment, a fiber optic pigtail 14 may be connected to the THz TX 10 and the THz RX 12. A fiber optic pigtail 14 is a short optical fiber that is permanently attached to a fiber optic device. This fiber optic device can include a source, a detector, a transmitter such as a THz TX 10, or another fiber optic device as is known to those skilled in the art. The pigtail 14 may be connected to the optical connector or a THz RX 14 at the other end.

System 2 may detect the constituents present in a sample 40 that has been inserted into a container 50. For example, a sample 40 may be a cork or other sealing apparatus for a sealed container such as but not limited to a wine bottle. In this embodiment, radiation 8 from a THz TX 10 propagates through both the container 50 and the sample 40. The radiation 8 propagates through a first lens 20, a first wall 52 of the container 50, the sample 40 and then through a second wall 54 of the container 50. The radiation 8 then passes through a second lens 21 before it is captured by a THz RX 12.

Alternatively, the radiation 8 may be propagated at an angle so that the radiation 8 is sent through the first wall 52 of the container 50, through the sample 40 and out the top of the sample 40 such that the radiation 8 never passes through the second wall 54 of the container 50.

Figure 3:
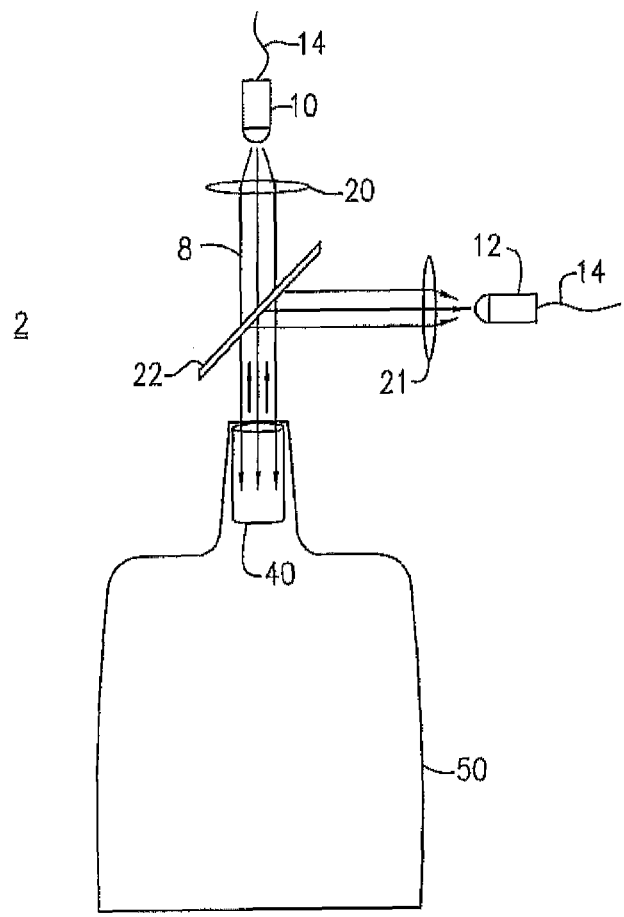
FIG. 3 depicts a schematic of a THz spectroscopy device adapted to scan a sample in accordance with at least one embodiment of the present invention.

Now referring to FIG. 3, in another embodiment of the present invention a system 2 is provided that detects constituents present in a sample 40 such as a sealing apparatus that has been inserted into a container 50. This embodiment differs from the embodiment of FIG. 2 in that radiation 8 from a THz TX 10 propagates solely through the sample 40 without passing through any part of the container 50. The radiation 8 from the THz TX 10 propagates through a first lens 20, then through an optical device such as a beamsplitter 22. The beamsplitter 22, which may be a partially reflecting mirror, allows the radiation 8 to pass through completely and propagate into the sample 40. Some of the radiation 8 then reflects back up through the sample 40 and back to the beamsplitter 22 which then acts as a directional coupler to direct the radiation 8 to a second lens 21 and then to a THz RX 12. Again, in additional embodiments, a fiber optic pigtail 14 may be operably connected to the THz TX 10 and the THz RX 12.

In another embodiment the present invention methods are provided to detect, identify and/or quantify constituents in a sample using THz technology. Methods are provided for detecting and/or identifying structural variations such as voids, structures, anomalies, defects, density variations or locations in the sample, such as a cork, in which bacteria, chemicals or mold could exist or propagate, and the identification and/or a determination of the likelihood that a constituent, subconstituent and/or contaminant is present.

In accordance with such methods, a signal or electromagnetic radiation in the THz frequency range from a THz source or THz transmitter is introduced. The signal or radiation that passes or propagates through the sample is then captured by a THz receiver. The receiver transmits the data, signal and/or THz absorption peaks to an analytic device for analysis and computation. The THz absorption peaks may then be compared to known THz absorption peak spectra for a determination of the constituents inside the sample.

The sample to be tested may be independent or acting as a sealing apparatus in a container. The apparatus used to practice the methods, including the THz source or the THz transmitter, the sample and the THz receiver, can be assembled in various configurations. The methods may employ apparatus such as those described hereinabove. For example, the methods may employ apparatus wherein the THz source and/or THz transmitter, the sample and the THz receiver are set up so that the radiation passes through one or more walls of the container and through the sample before being captured by the THz RX. One such configuration is a parallel configuration as depicted in FIG. 2.

In yet other embodiments, the methods may employ apparatus wherein radiation from the THz source and or THz transmitter pass through the sample and to the THz receiver without contacting the container as depicted in FIG. 3.

Examples and Experiments

In one example, the THz transmission of cork sample was measured employing apparatus as depicted in FIG. 1. A mode-locked Ti:sapphire laser was used to generate and detect pulses of THz radiation in micro-fabricated antenna structures. The pulse of Terahertz radiation was roughly a few picoseconds in duration and contains spectral components from about 0.1-2.5 THz. The THz radiation was focused to a ~1 mm spot size using lenses. The sample was placed at the focus of the radiation and mechanically scanned using computer controlled translation stages. After passing through the sample, the radiation was focused onto a THz detector. The image was acquired one pixel at a time; at each pixel, the spectrum of THz radiation was recorded.

Figure 4:
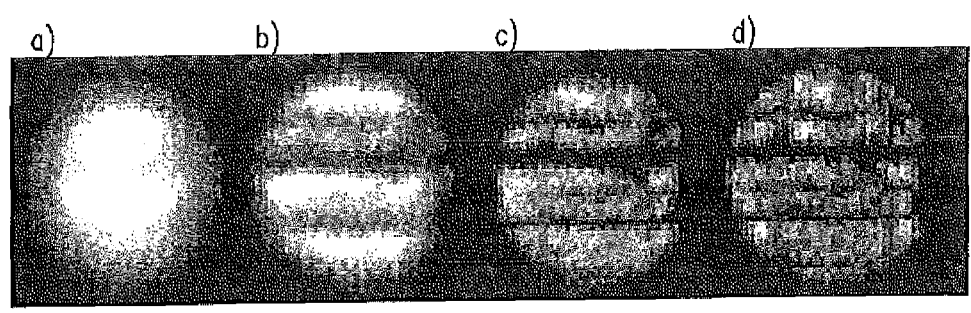
FIG. 4 depicts THz transmission images of the cork sample depicted in FIG. 5A for THz bandwidths as follows.
Figure 5A:
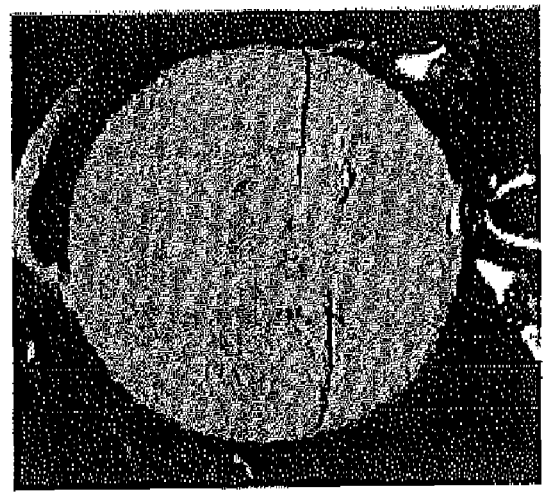
FIG. 5A is a photograph of a cork sample.

Now referring to FIG. 4, THz images were generated by measuring the THz power transmitted in a specific THz bandwidth. FIG. 4 depicts THz transmission images of the cork sample depicted in FIG. 5A for THz bandwidths as follows: FIG. 4a: 0.1-0.3 THz; FIG. 4b: 0.3-0.5 THz; FIG. 4c: 0.5-0.8 THz; and FIG. 4d 0.8-1.0 THz. Each pixel in the images is 500 μm square. The overall size of the THz cork image is ~19 mm. Bright pixels correspond to high transmission, while dark pixels correspond to low transmission. The THz image of the cork shows the internal structure of the cork, a 4.48 mm thick cork sample from a 1997 Riston Estates Cabernet Sauvignon as depicted in FIG. 5a.

Figure 5B:
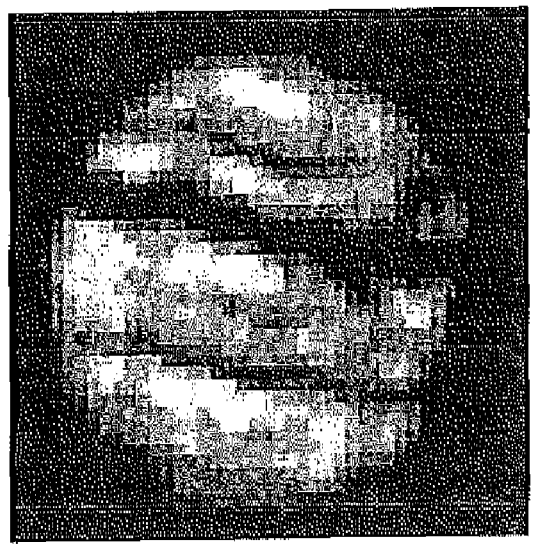
FIG. 5B is a THz transmission image of the cork sample of FIG. 5a using the same THz bandwidth as used in FIG. 4c.

Contrast in the image and the prominence of the internal structure depends on the band of THz frequencies used. The contrast in the THz image may be due to several effects in some embodiments; the two most common are absorption and scattering. Now referring to FIG. 5b, which is a THz transmission image of the cork sample of FIG. 5a using the same THz bandwidth as used in FIG. 4(c), except that the cork sample was dried overnight in a desiccant, it is observed that residual water trapped in the cork structure may affect absorption. The image after drying (FIG. 5b) illustrates that the apparent structure is still present.

Scattering of electromagnetic radiation can be thought of as occurring on two different spatial scales. When the size of the scattering object is much smaller than the wavelength of radiation (Rayleigh scattering), the scattering which is strongly wavelength dependent, scales as $v^4$ where $v$ is the electromagnetic frequency. When the wavelength is comparable to the size of the scattering object (Mie scattering), the efficiency of scattering is greatly enhanced and sensitive to the size of the scattering object.

Since the typical size of a cork cell (~40-60 μm) is much smaller than the wavelength the THz radiation used (1 THz corresponds to 300 μm, 0.1 THz corresponds to 3 mm), the observed contrast in the THz images as the THz frequency is increased, and the wavelength is decreased, is due to scattering of THz radiation by anomalies in the regular pattern of the cork cell structure. In some embodiments, anomalies may be lenticels or some structural defect in the cork cell pattern; or may be locations at which microorganisms and TCA could be concentrated due to the relative ease of transport of liquids and gases along the lenticels.

In accordance with another set of experiments, natural cork samples were acquired from a variety of bottled wine varietals. Samples were dried in ambient air for several days. Samples roughly 4 mm thick were cut from the end of the cork that was not in contact with the wine. As a control, samples of cork that had not been used in the bottling process were also tested.

Figure 6:
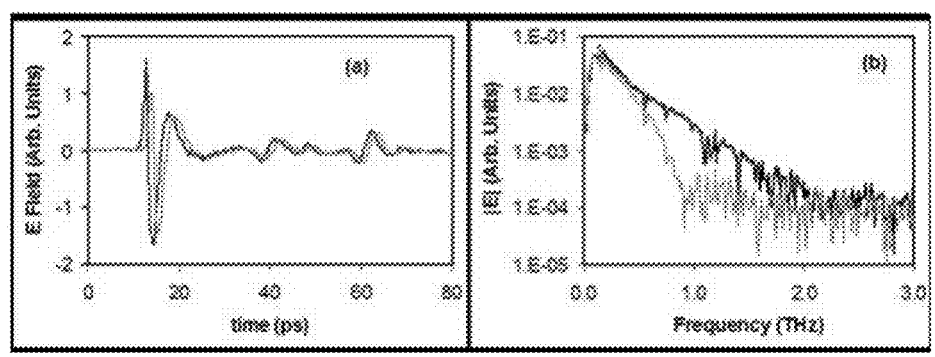
FIG. 6 depicts graphical representations of THz time-domain waveforms in accordance with at least one embodiment of the present invention.

A T-Ray 2000 Spectroscopy system (Picometrix, Inc) was used in the transmission mode to measure the THz time-domain waveform. Details of the THz time-domain method may be found in D. Mittleman, "Terahertz Imaging" in *Sensing with Terahertz Radiation*, D. Mittleman Ed. (Springer, 2003). A pair of silicon lenses (3 inch focal length) were employed to focus the THz radiation to a spot at which the sample was placed. The imaging system consisted of a pair of computer controlled linear translation stages (1 μm resolution). The THz images were acquired by recording the THz transmitted pulse at each sample position. Typical THz time-domain waveforms are shown in FIG. 6. Spectral information as a function of frequency, both phase and amplitude, was acquired through a Fourier transform of the time-domain data.

As shown in FIG. 6, the slight time shift in the arrival of the peak of the pulse is indicative of the real index of refraction of the cork sample. Typical values are between 1.07 and 1.1. In examining the magnitude of the THz electric field as a function of frequency, it is clear from the reference data that the THz amplitude approaches the noise limit of the THz system at approximately 2 THz. After passing through the cork sample, data beyond about 0.95 THz was in the noise for this particular sample location. For the spectroscopic data presented herein, only data within the signal-to-noise of the system is plotted for purposes of clarity.

THz images were formed by measuring the full time-domain waveform within an 80 ps time window. The sample was mechanically scanned in two directions at the focal point of the THz to generate an image one pixel at a time. Typical step sizes were 100-500 μm.

Results and Discussion

Figure 7:
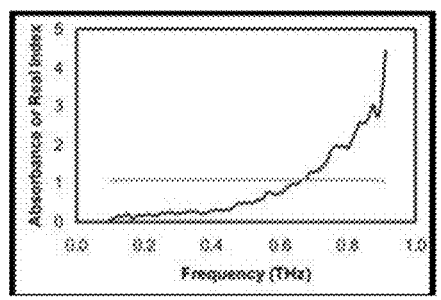
FIG. 7 is a graphical representation of the calculated frequency dependent absorbance (black) and the real index of refraction (gray) for the time-domain waveforms of FIG. 6.

There are many methods for analyzing the THz waveforms and generating a THz image. For example, one can measure the total transmitted THz power, the transmitted power within a given frequency interval, the change in the arrival time of the THz pulse, etc. At each pixel in the THz image, the THz phase and amplitude is normalized to the phase and amplitude of the reference waveform. FIG. 7 shows the corresponding absorbance $$-A(\nu) = ln(T(\nu))ln|E_s(\nu)|/|E_r(\nu)|)\mu L \quad (1)$$

at one pixel where $T(\nu)$ is the frequency dependent transmission referenced to a THz spectra with the sample removed. $|E_s|$ and $|E_r|$ are the magnitudes of the THz electric fields for the sample and reference, respectfully. L is the thickness of the sample and μ is defined as the attenuation coefficient.

FIG. 7 also shows the frequency dependence of the real index of refraction as calculated by $$n_{real}(\nu) = \frac{(\phi_r(\nu) - \phi_s(\nu))c}{2\pi\nu L} + 1 \quad (2)$$

where $\phi_s$ and $\phi_r$ are the Fourier transformed frequency dependant phases of the sample and reference waveforms, respectfully, c is the speed of light, L is the thickness of the sample, and ν is the frequency. The real index of refraction is essentially constant over the measured range.

The visible and typical THz images of cork samples are shown in FIGS. 8(a)-(d), 9(a)-(c), and 10(a)-(c). FIG. 8(a) is a front visible view of a cork, FIG. 8(b) is a back visible view of a cork and FIG. 8(c) is a 0.6-0.7 THz image through a 4.4 mm cork sample. Each pixel is 500 μm. The front view of the cork corresponds to the end that nominally would be in contact with the wine and the portion of the cork that could be visibly inspected. The visible image of the back side is reversed left to right for easier comparison to the THz image. The sample is oriented so that the grains of the cork are parallel to the bottom of the page. The image (0.9-1.0 THz transmission) of FIG. 8(d) is a high resolution (100 μm pixel) image of the area outlined in white.

Figure 8:
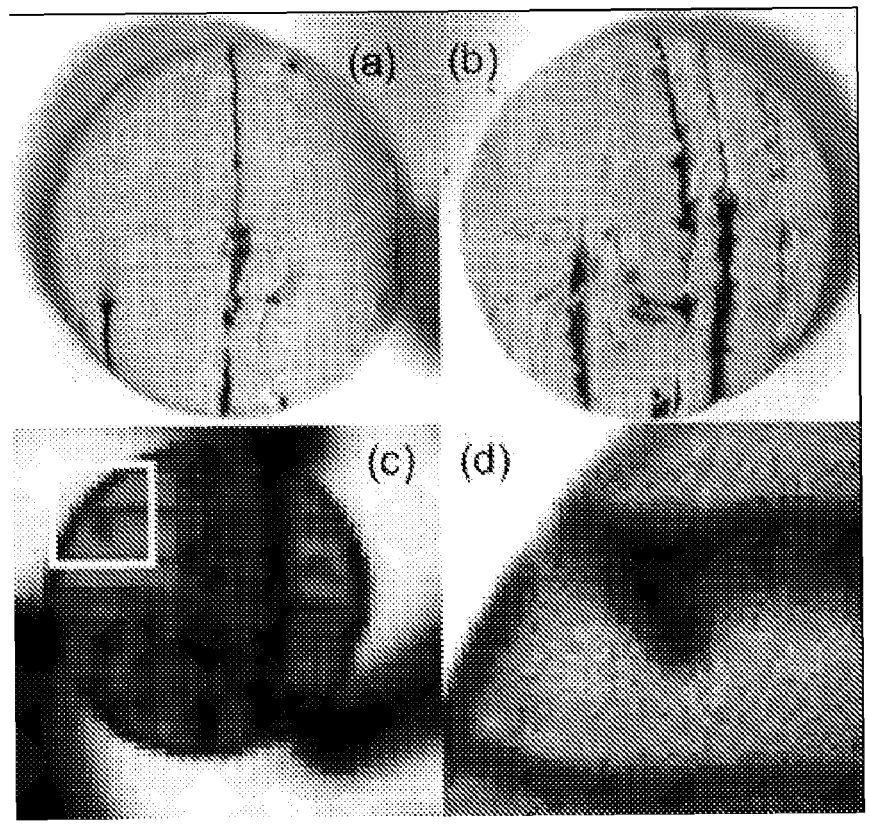

FIG. 9(a) depicts a front visible view of a different cork sample than that of FIG. 8. FIG. 9(b) is a back visible view of the cork of FIG. 9(a) and FIG. 9(c) is a THz image through a 4.35 mm sample from the cork of FIG. 9(a). The presence of cracks, void, and cork grain that are visible in the THz image of FIG. 9(c) would be overlooked in examining only the front visible image of FIG. 9(a).

Figure 10:
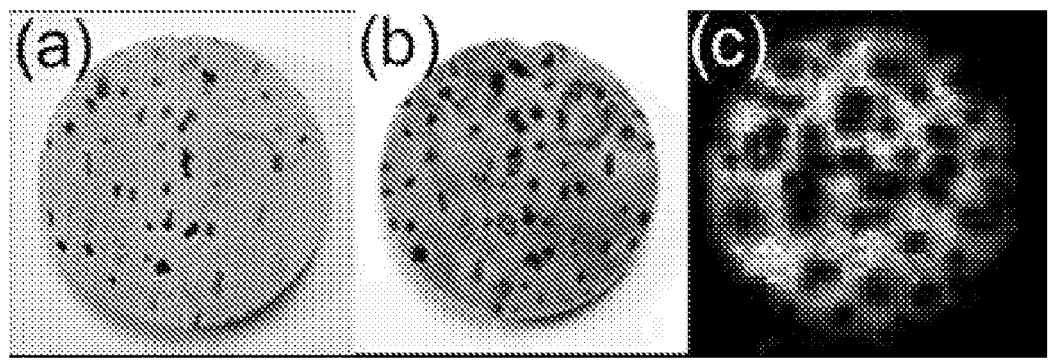

FIG. 10(a) depicts a front visible view of another cork sample. FIG. 10(b) depicts a back visible view of the cork of FIG. 10(a) and FIG. 10(c) is a THz images through a 4.02 mm sample from the cork of FIG. 10(a). FIG. 10(c) shows the images of a hole (bright spot) and cavities (dark spots).

The THz images 8(c), 9(c) and 10(c) were formed by calculating the average transmitted power in the 0.9-1.0 THz frequency band. The sample holder, which is made of aluminum, appears dark in the image since it blocks THz radiation. The sample was oriented so that the grain structure of the cork was disposed roughly parallel to the bottom of the page.

Figure 9:
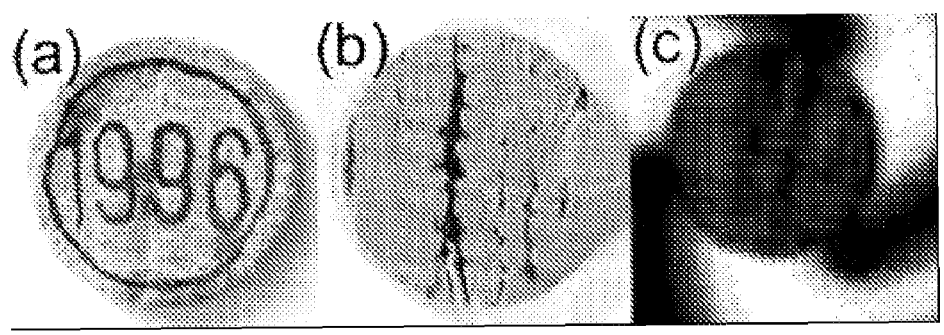

In comparing the visible and THz images, it is clear that the THz images show the presence of the cork grain as well as the presence of defects and voids. In examining only the front visible image as shown in FIG. 8(a), one would be led to the false assumption that the cork sample of FIG. 8 was fairly uniform with only one large crack in the middle of the sample, and a smaller one in the lower left corner. The THz image of FIG. 8(c) reveals defects that are not apparent on mere visual inspection. Likewise, in examining the front visible image shown in FIG. 9(a) of the cork sample of FIG. 9 one would be led to the false conclusion that the cork is defect free. However, the THz image in FIG. 9(c) shows the presence of three major cracks/voids in the first 4.35 mm of cork. Since the THz radiation transmits through the cork and enables one to nondestructively evaluate the interior structure, the THz image shows the presence of a larger number of cracks and voids that would nominally be invisible if one where to simply visibly inspect the cork surfaces.

Figure 11:
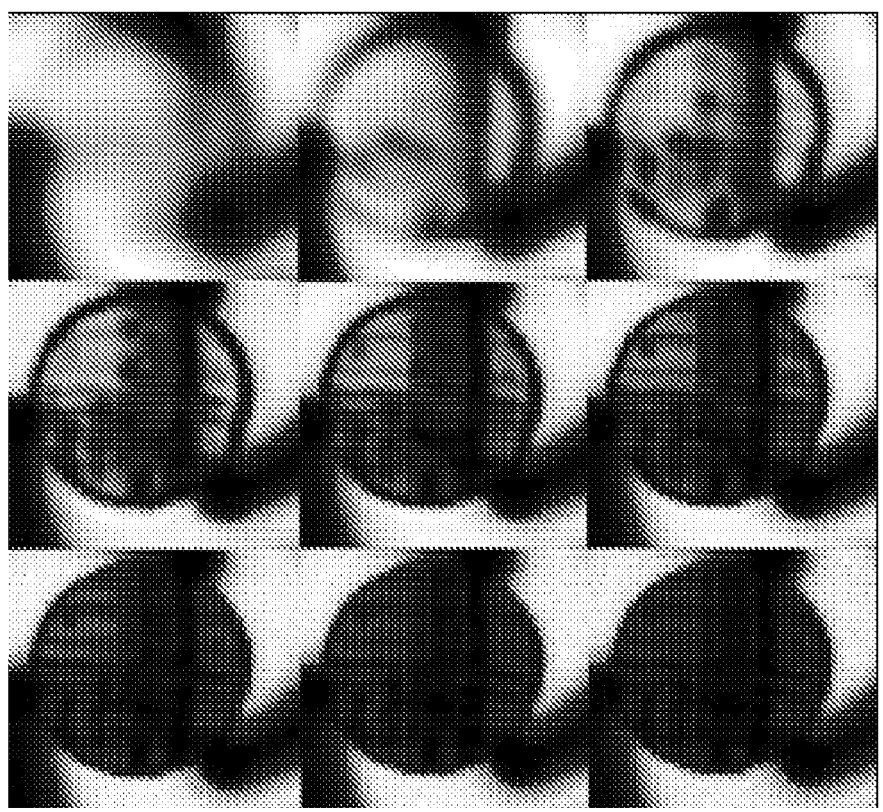
FIG. 11 depicts THz transmission images of the cork of FIG. 9 in 0.1 THz bandwidths from 0.1-0.2 THz through 0.9-1.0 THz (left to right, top to bottom progression). Each pixel is 500 μm.

Now referring to FIG. 11, the THz transmission images of the cork of FIG. 9 are depicted in 0.1 THz bandwidths. The frequency range is 0.1-0.2 THz for the top left image and 0.9-1.0 THz for the bottom right image. As the THz frequency increases, the spatial resolution improves. This is expected since one would expect the spatial resolution to degrade with increasing THz wavelength (decreasing THz frequency) due to diffractive effects. It is also interesting to note that the contrast of the image appears to change as a function of frequency. For example, while all of the vertical cracks are visible in the 0.9-1.0 THz image, portions of those cracks are missing in the 0.5-0.6 THz images. Moreover, fairly high transmission regions, particularly in the upper left quarter of the sample, are prevalent in the THz images below 0.7 THz, but are absent for THz images above 0.7 THz. As will be discussed below, the THz radiation interacts differently with the cracks, voids, and grains creating the contrast in the THz images.

Figure 12:
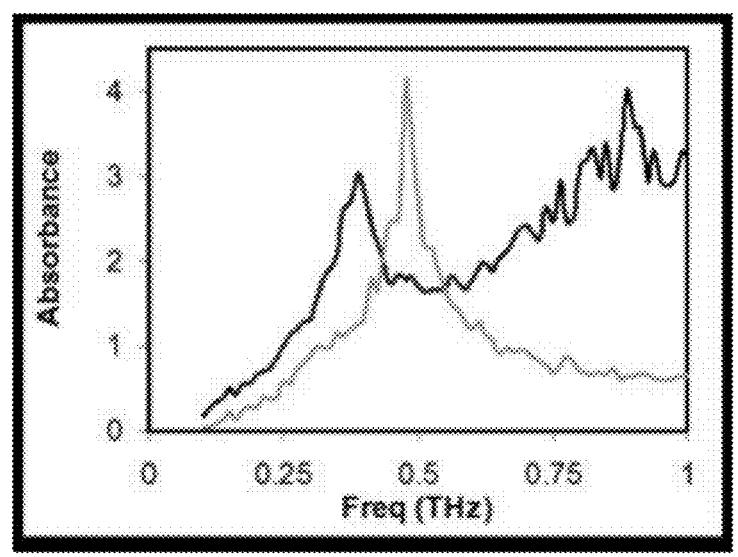
FIG. 12 is a graphical representation of the absorbance spectra of a sample in accordance with at least one embodiment of the present invention.

In order to understand the differences in the darker features of FIG. 8 and FIG. 11, the spectral shape of the absorbance at various positions of the sample was examined. The presence of the large voids and cracks are characterized by spectral peaks in the absorbance as illustrated in FIG. 12. FIG. 12 depicts absorption spectra (black) from pixel position (x37, y42) of FIG. 8c corresponding to a large crack/void in the THz cork image. The presence of a sharp feature near 0.39 THz is observed. Corresponding spectra (gray) from pixel position (x13,y51) corresponds to the edge of the cork. An anomalous spectral peak appears near 0.47 THz.

While the location of the spectral peak may vary between 0.3 and 0.5 THz at different positions of the cracks/void, the peak is always present. For the edge of the cork, the peak position varies between 0.4-0.6 THz depending on location. Without being restricted to a single theory, it is believed that the absorbance peaks of FIG. 12 are an artifact of enhanced scattering of the THz radiation by the presence of boundaries or cracks/voids.

In examining locations on the sample for which there are no edges or voids or cracks, one observes in the THz images the presence of dark and clear bands parallel to the direction of the grain structure. The absorbance spectra at these locations typically do not exhibit any spectral peaks but rather an increasing absorbance with frequency that may be fit to a power law dependence $$A(v)=Cv^m B \tag{3}$$

where $A(v)$ is the frequency dependent absorbance, $v$ is the THz frequency, and C, B, and m are fit parameters. Within the same dark or light band, there is some variation in the extracted parameters, but the spectral shape of the absorbance is consistent within the same dark or light band.

In order to gauge the range of extracted parameters, the THz absorption spectra are analyzed for different light and dark grains. Table I summarizes the data for several different corks.

TABLE I

Summary of extracted parameters from power law dependence of absorbance spectra

| Sample | Light grain | | Dark grain | | Cavity | |
|---|---|---|---|---|---|---|
| | C | m | C | m | C | M |
| FIG. 3 | 0.85 ± 0.13 | 1.46 ± 0.43 | 2.40 ± 0.82 | 2.33 ± 0.82 | — | — |
| FIG. 4 | 1.37 ± 0.08 | 1.64 ± 0.39 | 2.09 ± 0.68 | 1.76 ± 0.43 | — | — |
| FIG. 5 | 1.31 ± 0.48 | 1.11 ± 0.29 | — | — | 4.63 ± 0.54 | 1.33 ± 0.75 |

The average and uncertainty of the values for the C or m coefficients were determined by the average and standard deviation for the set of 10 measurements on each cork sample. In comparing grains from the same cork, both the C and m coefficients increase from light to dark grains. This increase is indicative of enhanced THz scattering in the dark grains.

THz images can also be generated based on the time-delay in the arrival of the THz pulse or analogously the frequency dependent phase of the THz wave. While time-delay and phase THz images (not shown) show the presence of similar structures as the THz amplitude images, the contrast is considerably degraded. Since the arrival time is determined by the optical path length (i.e., the product of the real index of refraction and the physical thickness of the sample), one would expect the contrast in a time-delay or phase image to be a result of either local variations in the thickness of the sample or variations in the real index of refraction. From THz phase images, the estimated change in the optical path length between light and dark grains is approximately 30 μm. In comparison, the size of a cork cell is approximately 36-50 μm. The fact that the time-delay of the THz pulse through the sample is essentially independent of position further suggests that the contrast in the amplitude images is essentially due to scattering rather than an intrinsic absorption.

Since the size of the cork cells (~36-50 μm) approaches the wavelength of the THz radiation (1 THz corresponds to a 300 μm wavelength) as the THz frequency increases, the frequency dependent absorbance can be modeled with Mie scattering theory for regions of the cork which are free of defects and voids. THz absorbance by small particles can be modeled by Mie scattering theory. In particular, in the weakly scattering limit, Mie scattering produces a power law frequency dependent absorbance.

If the sample is assumed to consist of spherical scatterers, the attenuation coefficient (μ in Eq. (1)) in Mie theory takes on the following form $$\mu_{th} = N \frac{c^2}{2\pi v^2} \sum_{m=1}^{\infty} (2m+1) \text{Re}(a_m + b_m) \tag{4}$$

where N is the number of scattering centers per unit volume, c is the speed of light and $a_m$ and $b_m$ are the coefficients in the infinite summation such that $$\begin{cases} a_m = \dfrac{\psi'_m(y)\psi_m(x) - n\psi_m(y)\psi'_m(x)}{\psi'_m(y)\zeta_m(x) - n\psi_m(y)\zeta'_m(x)} \\ b_m = \dfrac{n\psi'_m(y)\psi_m(x) - \psi_m(y)\psi'_m(x)}{n\psi'_m(y)\zeta_m(x) - \psi_m(y)\zeta'_m(x)} \end{cases} \text{where} \begin{cases} \psi_m(z) = z j_m(z) \\ \zeta_m(z) = z h_m^{(2)}(z). \end{cases} \tag{5}$$

Here $j_n(z)$ and $h_m^{(2)}(z)$ are Spherical Bessel functions of the first kind and third kind respectively when z can be either $x=2\pi v r/c$ or $y=2\pi v n r/c$, r is the radius of the spherical grain, and n is the frequency independent refractive index.

In applying this model to natural cork, we note that several approximations are assumed. For example, cork cells are not spherical, but rectangularly shaped. Moreover, the cork cell itself is not homogeneous, but rather a cell wall surrounding trapped gases. For the purposes of this simple model, we assumed that the cork cell is uniform with a real index of refraction given by the THz spectroscopy measurements (~1.07-1.1).

Figure 13:
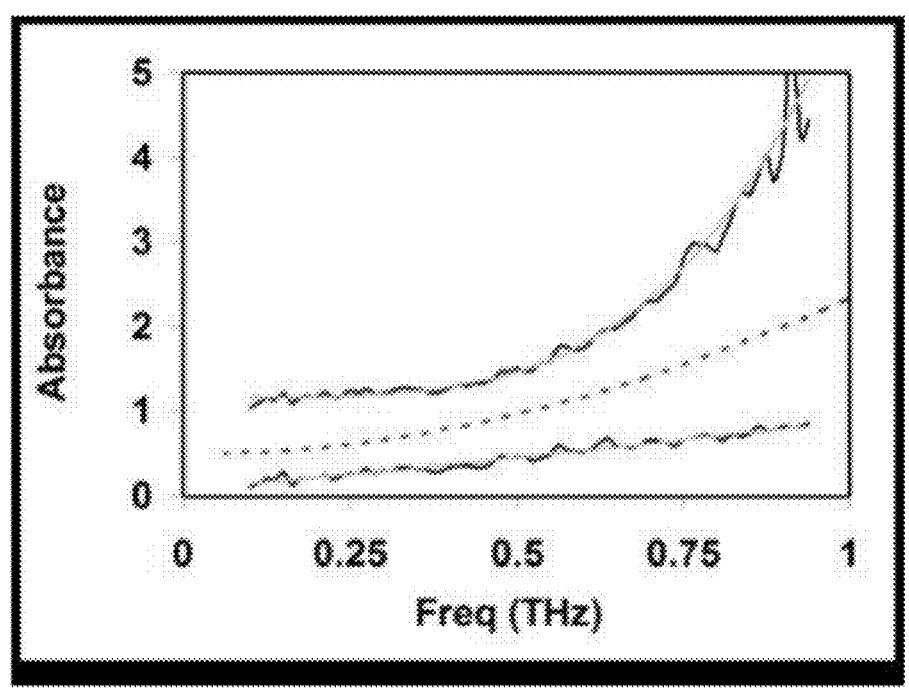
FIG. 13 is a graphical representation of the absorbance spectra of a sample in accordance with at least one embodiment of the present invention.

Using a microscope to inspect the cork cells, we found that the cells are roughly 36 μm in size, and exhibit a regular rectangular-like shape that is typical of cork cells. Using the Mie scattering model of Eq. (4)-Eq. (5) above, we estimated the frequency dependence of the absorbance for particles with index of refraction 1.07, sample thickness 4.4 mm and particle sizes of r=18 μm corresponding roughly to the size of the cork cell. N, the number of particles per unit volume, was estimated based on the volume of a cork cell to be $N \sim 2 \times 10^{13}$. The estimated absorbance is shown in FIG. 13. FIG. 13 depicts measured absorbance (upper black curve) from pixel position (x15,y34) of FIG. 8 (vertically offset by 1.0) corresponding to a dark grain in the cork THz image. The gray curve is a power law fit to the data using Eq. (3). The extracted parameters are: C=4.844, m=4.002, B=0.1636. The bottom curve is the absorbance spectra from pixel position (x14,y32) corresponding to a clear grain in the cork THz image. The extracted parameters are: C=0.7924, m=1.126, B=0.09013. The dashed curve (vertically offset by 0.5) is the predicted absorbance of 18 μm radius particles. The index of refraction is 1.1, sample thickness 4.4 mm, and the number of particles per volume is $2\times10^{13}$ m$^{-3}$. Fitting this dashed curve to a power law dependence yields fitting parameters from Eq. (3) of A=1.837, m=1.91. We note that these parameters are comparable to the parameters extracted from the THz absorbance data for the cork sample of FIG. 8.

In order to understand the origin of the contrast in dark and light THz grains, possible changes in the cell structure or density that could modify the efficiency of scattering should be considered. Typically during the spring, cork trees grow more rapidly (spring wood) and the cork cells are larger. In comparison, the new cells that are formed during the summer growth are smaller (summer wood) and more densely packed. Moreover, as the tree grows radially and the diameter of the tree expands, the regular pattern of cells can not be maintained. Consequently, a disruption in the regularity of the cell structure occurs leading to cracks, voids, or a change in grain structure. Either an increase in cell size or disruption in the grain structure could lead to increased THz scattering and explain the observed contrast in the THz images.

Based on the foregoing it is apparent THz imaging employing the present methods and apparatus for sample evaluation is superior to visual inspection by human experts and camera systems, which can only inspect the surface of a sample such as a cork. THz imaging enables evaluation of the internal structure of the cork as well as the surface structure. For example, the spatial resolution of the camera system reported in J. Chang, et al., "Cork quality classification system using a unified image processing and fuzzy-neural network methodology," IEEE Trans Neural Networks 8, 964-974 (1997) images the end of a cork with approximately 90 by 90 pixels. The THz images of the end of the cork are roughly 45 by 45 pixels corresponding to 0.5 mm spatial resolution. The maximum resolution is determined by the step size of each pixel as well as the THz frequency. Since the spatial resolution of free-space optical system is typically limited by diffractive effects to be on the order of the wavelength of light, one would expect that the resolution limit of 1 THz radiation would be on the order of 300 μm. Therefore, halving the pixel step size to 250 μm in the THz images would give approximately the same spatial resolution as the visible images of the aforementioned camera system but with the added advantage of probing the interior structure of the cork.

By way of further comparison, as described in A. Brunetti et al., "Cork quality estimation by using Compton tomography," Nuclear Instruments and Methods in Physics Research Section B: Beam Interactions with Materials and Atoms 196, 161-168 (2002), an x-ray transmission geometry does not produce good contrast x-ray images. The poor contrast results from the fact that the interaction between the x-rays and cork is very weak so that there is very little loss of x-ray power in going through the natural cork cells and the voids. This is in contrast with the THz transmission imaging methods and apparatus of the present invention which provides for a strong interaction between the THz radiation and the cork cell structure due to Mie scattering: the size of the cork cells is comparable to the wavelength of the probing radiation. THz radiation, as compared to x-rays, is more efficiently scattered by the cells and voids indicating that THz imaging is a much more sensitive method for imaging the internal structure of the cork. The x-ray tomography technique described in Brunetti et al. measures scattered x-rays by placing the x-ray receiver approximately perpendicular to the incoming direction of the probing x-rays. Regions of high electron density more efficiently scatter the x-rays resulting in contrast between the cork and voids. The x-ray beam is collimated to a diameter of roughly 1 mm and passed through the sample. Since the spatial resolution of the x-ray method is limited to roughly 1 mm (as determined by the diameter of the probing x-ray beam), the spatial resolution of the THz system is inherently superior to the x-ray method described in Brunetti et al. Moreover, a two-dimensional linear scan as well as a rotational scan is required to reconstruct the x-ray tomography images. Since THz radiation interacts much more strongly with the cork cell structure through Mie scattering, a simple transmission image requires only a 2-D linear scan.

Moreover, the present methods and apparatus may be used to distinguish between mature cork and green cork (higher concentration of water or cytoplasmic liquid). Since water and liquids in general highly reflect THz radiation, green cork is will efficiently reflect/attenuate THz radiation compared to mature cork.

The presently described method has various applications. One embodiment of the application is to identify wine that has been corked. Other embodiments of the application are to identify contamination or spoilage of other products, including but not limited to oils, such as pressed extra virgin olive oil that is bottled and sealed with a natural cork, or vinegar. Other embodiments include identifying the proper fermentation of, by way of example only, beer, mead, sauerkraut or kim chi, or aging of food products such as cheese has occurred. These examples are merely illustrative of possible additional applications of the presently described method and can be in no way construed as a limitation of the use thereof.

Applicants have attempted to disclose all embodiments and applications of the described subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All references cited herein are incorporated fully by reference. The following references are also hereby incorporated fully by reference:

J. Chang, G. Han, J. M. Valverde, N. C. Griswold, J. F. Duque-Carrillo, and E. S'anchez-Sinencio, "Cork quality classification system using a unified image processing and fuzzy-neural network methodology," IEEE Trans Neural Networks 8, 964-974 (1997).

R. Juanola, D. Subirà, V. Salvado, J. A. Garcia Regueiro and E. Anticò, "Evaluation of an extraction method in the determination of the 2,4,6-trichloroanisole content of tainted cork," J. Chromatography A 953, 207-14 (2002).

E. Lizarraga, Á. Irigoyen, V. Belsue and E. González-Peñas, "Determination of chloroanisole compounds in red wine by headspace solid-phase microextraction and gas chromatography-mass spectrometry," J. Chromatography A 1052, 145-9 (2004).

E. Herve, S. Price, G. Burns, P. Weber, presented at the ASEV Annual Meeting, Reno, Nev., 2 Jul. 1999. http://www-.corkqc.com/asev/asev2-2.htm.

A. Brunetti, R. Cesareo, B. Golosio, P. Luciano and A. Ruggero, "Cork quality estimation by using Compton tomography," Nuclear Instruments and Methods in Physics Research Section B: Beam Interactions with Materials and Atoms 196, 161-168 (2002).

D. Zimdars, J. S. White, G. Stuk, A. Chernovsky, G. Fichter, and S. Williamson, "Large area terahertz imaging and nondestructive evaluation applications," Insight-Non-Destructive Testing and Condition Monitoring 48, 537-539 (2006).

D. Zimdars, J. A. Valdmanis, J. S. White, G. Stuk, W. P. Winfree, and E. I. Madaras, "Time domain terahertz detection of flaws within space shuttle sprayed on foam insulation" in *Conference on Lasers and Electro-Optics/Quantum Electronics and Laser Science and Photonic Applications Systems Technologies*, Technical Digest (CD) (Optical Society of America, 2004), paper CThN4. http://www.opticsinfobase.org/abstract.cfm?id=104293.

H. S. Chua, P. C. Upadhya, A. D. Haigh, J. Obradovic, A. A. P. Gibson, and E. H. Linfield, "Terahertz time-domain spectroscopy of wheat grain" in *Conference Digest of the 2004 Joint 29th International Conference on Infrared and Millimeter Waves and 12th International Conference on Terahertz Electronics* (Institute of Electrical and Electronics Engineers, New York, 2004), pp 399-400; H. S. Chua, J. Obradovic, A. D. Haigh, P. C. Upadhya, O. Hirsch, D. Crawley, A. A. P. Gibson, and E. H. Linfield, "Terahertz time-domain spectroscopy of crushed wheat grain" in 2005 *IEEE MTT-S International Microwave Symposium* (Institute of Electrical and Electronics Engineers, New York, 2005), p 4.

S. Hadjiloucas, L. S. Karatzas, and J. W. Bowen, "Measurements of leaf water content using terahertz radiation," IEEE Trans. Microwave Theory and Techniques 47, 142-149 (1999); S. Hadjiloucas, R. K. H. Galvao, J. W. J. Bowen, "Analysis of spectroscopic measurements of leaf water content at terahertz frequencies using linear transforms", Opt. Soc. Am. A 19, 2495-2509 (2002).

M. Reid and R. Fedosejevs, "Terahertz birefringence and attenuation properties of wood and paper," Applied Optics 45, 2766-2772 (2006).

C. J. Strachan, T. Rades, D. A. Newnham, K. C. Gordon, M. Pepper, and P. F. Taday, "Using terahertz pulsed spectroscopy to study crystallinity of pharmaceutical materials," Chem. Phys. Lett. 390, 20-24 (2004).

D. S. Venables and C. A. Schmuttenmaer, "Spectroscopy and dynamics of mixtures of water with acetone, acetonitrile, and methanol," J Chem. Phys. 113, 11222-36 (2000).

J. F. Federici, B. Schulkin, F. Huang, D. Gary, R. Barat, F. Oliveira, and D. Zimdars, "THz imaging and sensing for security applications-explosives, weapons and drugs," Semicond. Sci. Technol. 20, S266-80 (2005).

J. F. Federici, D. Gary, R. Barat, Z.-H. Michalopoulou, 'Detection of Explosives by Terahertz Imaging', in *Counter-Terrorism Detection Techniques of Explosives* Jehuda Yinon Ed. (Elsevier, 2007).

F. C. Delucia, "Spectroscopy in the Terahertz Spectral Region", in *Sensing with Terahertz Radiation*, D. Mittleman Ed. (Springer, 2003).

M. C. Beard, G. M. Turner, and C. A. Schmuttenmaer, "THz Spectroscopy," J. Phys. Chem B 106, 7146-7159 (2002).

F. Huang, B. Schulkin, H. Altan, J. Federici, D. Gary, R. Barat, D. Zimdars, M. Chen and D. Tanner, "Terahertz study of 1,3,5-trinitro-s-triazine by time-domain and Fourier transform infrared spectroscopy," Appl. Phys. Lett, 85, 5535-7 (2004).

A. Nystrom, A. Grimvall, C. Krantz-Rulcker, R. Savenhed, K. Akerstrand, "water off-flavour caused by 2,4,6-trichloroanisole," Water Science and Technology 25, 241-49 (1992).

S. Karlsson, S. Kaugare, A. Grimvall, H. Boren, R. Savenhed, "Formation of 2,4,6-trichlorophenol and 2,4,6-trichloroanisole during treatment and distribution of drinking water," Water Science and Technology 31, 99-103 (1995).

A. Miki, A. Isogai, H. Utsunomiya, H. Iwata, "Identification of 2,4,6-trichloroanisole (TCA) causing a musty/muddy off-flavor in sake and its production in rice koji and moromi mash," J. Bioscience and Bioengineering 100, 178-83 (2005).

L. H. Aung, J. L. Smilanick, P. V. Vail, P. L. Hartsell, E. Gomez, "Investigations into the Origin of Chloroanisoles Causing Musty Off-Flavor of Raisins," J. Agricultural and Food Chemistry 44, 3294-96 (1996).

C. Silva Pereira, J. J. Figueiredo Marques, M. V. San Romao, "Cork taint in wine: Scientific knowledge and public perception—A critical review," Critical Reviews in Microbiology 26, 147-62 (2000).

A. P. Pollnitz, K. H. Pardon, D. Liacopoulos, G. K. Skouroumounis, M. A. Sefton, "The analysis of 2,4,6-trichloroanisole and other chloroanisoles in tainted wines and corks," Australian J. Grape and Wine Research 2, 184-90 (1996).

J. Gunschera, F. Fuhrmann, T. Salthammer, A. Schulze, E. Uhde, "Formation and emission of chloroanisoles as indoor pollutants," Environmental Science and Pollution Research 11, 147-51 (2004).

J. Prescott, L. Norris, M. Kunst, S. Kim, "Estimating a 'consumer rejection threshold' for cork taint in white wine," Food Quality and Preference 16, 345-49 (2005).

D. Mittleman, "Terahertz Imaging" in *Sensing with Terahertz Radiation*, D. Mittleman Ed. (Springer, 2003).

D. M. Mittleman, S. Hunsche, L. Boivin, M. C. Nuss, "T-ray tomography," Optics Letters 22, 904-6 (1997).

T. Yasui, T. Yasuda, T. Araki, E. Abraham, "Real-time two-dimensional terahertz tomography of moving objects," Optics Comm. 267, 128-36 (2006).

H. Zhong, J. Xu, X. Xie, T. Yuan, R. Reightler, E. Madaras, and X.-C. Zhang, "Nondestructive defect identification with terahertz time-of-flight tomography," IEEE Sensors Journal 5, 203-8 (2005).

What is claimed is:

1. A method of nondestructively detecting at least one constituent in an interior portion of a sample by THz imaging of at least a portion of the interior of the sample comprising:
   introducing THz radiation to a sample;
   receiving the THz radiation transmitted through the sample;
   collecting spectral data of the received THz radiation comprising acquiring the image one pixel at a time and recording the spectrum of THz radiation at each pixel; and
   generating a THz image of at least a portion of the interior of the sample by measuring one of THz power transmitted in a specific THz bandwidth, total transmitted THz power, or the frequency dependent phase of a THz wave, wherein the THz image contains information predictive of the presence or absence of a constituent, wherein the constituent is at least one of a void, anomaly, defect, density variation, or location in which a chemical or biological entity could exist or propagate.

2. The method defined in claim 1 further including the step of measuring amplitude and phase components of the received THz radiation.

3. The method of claim 1 wherein the sample is a cork.

4. The method of claim 1 comprising analyzing absorption spectra from a portion of the image.

5. The method of claim 1 comprising analyzing absorption spectra of at least one pixel of the image for determining at least one of whether a constituent is present in the sample, the identity of a constituent in the sample or the quantity or amount of a constituent in a sample.

6. The method of claim 1 comprising analyzing absorption spectra of more than one pixel of the image for determining at least one of whether a constituent is present in the sample, the identity of constituent in the sample or the quantity or amount of a constituent in a sample.

7. A method for nondestructively detecting a constituent in the interior of a sample containing cork, wherein the constituent is at least one of a void, anomaly, defect, density variation, or location in which a chemical or biological entity could exist or propagate, the method employing THz radiation to generate a THz image of at least a portion of an interior of the cork comprising the steps of:
  introducing THz radiation to the sample;
  acquiring spectral information from the THz radiation as a function of frequency through a Fourier transform of time-domain data; and
  scanning the sample to generate an image one pixel at a time and forming a THz image by measuring one of THz power transmitted in a specific THz bandwidth, total transmitted THz power, or the frequency dependent phase of a THz wave.

8. A THz spectroscopy apparatus adapted to detect a constituent, selected from at least one of a void, anomaly, defect, density variation, or location in which a chemical or biological entity could exist or propagate, located in an interior of a sample comprising:
  a source configured to generate THz radiation for introduction to the sample;
  a receiver configured to receive THz radiation transmitted through the sample;
  a device adapted to collect spectral data from the received THz radiation;
  a means for producing a THz image of at least a portion of the interior of the sample by measuring one of THz power transmitted in a specific THz bandwidth, total transmitted THz power, or the frequency dependent phase of a THz wave; and
  a device adapted to analyze an absorption spectra of at least a portion of the THz image.

9. The apparatus of claim 8 adapted to generate a THz pulse having a duration in a range from about 1 femtosecond to about 100 nanoseconds.

10. The apparatus of claim 8 further comprising at least one lens adapted to focus the generated THz radiation on the sample.

11. The apparatus of claim 8 further comprising at least one lens adapted to direct the received THz radiation to a THz detector.

12. The apparatus of claim 8 further comprising a beamsplitter and optionally a fiber optic pigtail.

* * * * *